United States Patent [19]

Iles

[11] Patent Number: 5,306,469
[45] Date of Patent: Apr. 26, 1994

[54] SAMPLE CONTAINER HOLDER

[75] Inventor: Kenneth E. Iles, Los Altos, Calif.

[73] Assignee: Abbott Laboratories, Abbott Park, Ill.

[21] Appl. No.: 86,744

[22] Filed: Jul. 2, 1993

[51] Int. Cl.$^5$ .............................................. B01L 9/06
[52] U.S. Cl. ............................ 422/104; 422/99;
422/100; 422/102; 436/809; 436/810; 206/562;
206/563; 211/74; 435/809
[58] Field of Search ............... 422/99, 100, 102, 104;
436/809, 810; 206/443, 446, 522, 562, 563;
211/74, 89; 435/296, 298, 809; 277/34.3, 34.6

[56] References Cited

U.S. PATENT DOCUMENTS

| | | | |
|---|---|---|---|
| 2,630,233 | 3/1953 | Kircher | 211/74 |
| 3,456,783 | 7/1969 | Clark | 206/65 |
| 3,593,873 | 7/1971 | Vonk | 220/21 |
| 3,819,081 | 6/1974 | Runte | 206/446 X |
| 4,073,620 | 2/1978 | Gray et al. | 23/253 R |
| 4,180,272 | 12/1979 | Heitz | 277/28 |
| 4,306,665 | 12/1981 | Hickey | 277/34.3 X |
| 4,510,119 | 4/1985 | Hevey | 422/71 |
| 4,874,102 | 10/1989 | Jessop et al. | 422/102 X |
| 4,913,286 | 4/1990 | Tate | 206/329 |
| 4,932,533 | 6/1990 | Collier | 206/569 |
| 4,963,493 | 10/1990 | Daftsios | 435/287 |
| 5,096,078 | 3/1992 | McQueeny | 206/522 X |
| 5,102,150 | 4/1992 | Kahn | 277/34.3 |

Primary Examiner—James C. Housel
Assistant Examiner—Harold Y. Pyon
Attorney, Agent, or Firm—Richard D. Schmidt

[57] ABSTRACT

A holder is pneumatically actuated to grasp and hold a plurality of sample containers during an analytical process which requires movement of the containers. The holder comprises a body having holes therein for receiving the caps and upper portions of the containers. Within each hole is a rigid cylindrical element and within each rigid element is a flexible tubular element. The outer diameter of the flexible element is smaller than the inner diameter of the rigid element so that a pneumatically sealed chamber is formed between the two elements when the ends of the flexible element are folded back over the ends and outer surface of the rigid element. The holder body and the rigid element are provided with holes forming a fluid passage through which positive and negative pressures may be applied to the chamber. When a negative pressure is applied to the chamber to draw the flexible element outward toward the rigid element, the cap and upper portion may move freely into the flexible element. When a positive pressure is applied to the chamber to expand the chamber by moving the flexible element inwardly, the flexible element grips both the cap and upper portion of a container thereby reducing the chances that the cap and container will separate.

14 Claims, 4 Drawing Sheets

SAMPLE CONTAINER HOLDER

FIELD OF THE INVENTION

The present invention relates to a holder suitable for use in automated analytic systems. More particularly, the invention relates to a holder for gripping and holding sample containers as the containers are transported or are inverted to mix or agitate their contents.

BACKGROUND OF THE INVENTION

Holders now used in the field of automated clinical analysis employ mechanical grip devices for gripping sample containers after the holders are lowered over the upper portions of the containers. In addition to often being complex and hard to clean, mechanical grippers have other disadvantages. They do not readily accommodate sample containers having different diameters or varying cap configurations. Furthermore, in the event of a power failure, a mechanical gripper may lose its grip thus dropping the containers and spilling their contents.

A further disadvantage exists when a holder with a mechanical grip device is employed in a mixer or shaker device which inverts the holder and the containers in order to mix the contents of the containers. Since a mechanical gripper grips the upper portion of the sample containers but not their caps, a cap may separate from a container during the inverting process thereby spilling the container contents.

SUMMARY OF THE INVENTION

An object of the present invention is to provide a sample container holder which is easy to clean and is capable of handling sample containers having different diameters and/or different cap configurations.

A further object of the invention is to provide a sample container holder which requires no adjustment in order to handle sample containers having different diameters and/or different cap configurations.

Another object of the invention is to provide a sample container holder having a fail-safe mode of operation such that the sample containers are positively gripped in the event of a power failure.

Still another object of the invention is to provide a sample container holder which grips both the sample containers and their caps so that, upon inversion of the holder, the caps will not separate from the containers.

A holder according to the present invention comprises a body having holes therein for receiving the caps and upper portions of sample containers. Within each hole is a rigid cylindrical element and within each rigid element is a tubular flexible element having a diameter smaller than that of the rigid element. The ends of the flexible element are folded back over the ends of the rigid element to form an hermetically sealed chamber. Near the bottoms of the holes are ledges which retain the elements within the holes and a cover closes the tops of the holes. The cover presses on the folded-over top portions of the flexible elements thereby forming pneumatically sealed regions between the walls of the holes and the outer surfaces of the rigid elements. The body and the rigid elements are provided with openings communicating with the pneumatically sealed regions so that positive and negative pressure may be applied to the chambers. The diameter of the flexible elements is chosen such that when either ambient or a positive pressure is present in a chamber, the flexible element will grip a container and its cap.

Other objects and advantages of the invention, its mode of operation and the method of making it will become obvious upon consideration of the following description and the accompanying drawings.

DETAILED DESCRIPTION

Figure 1:
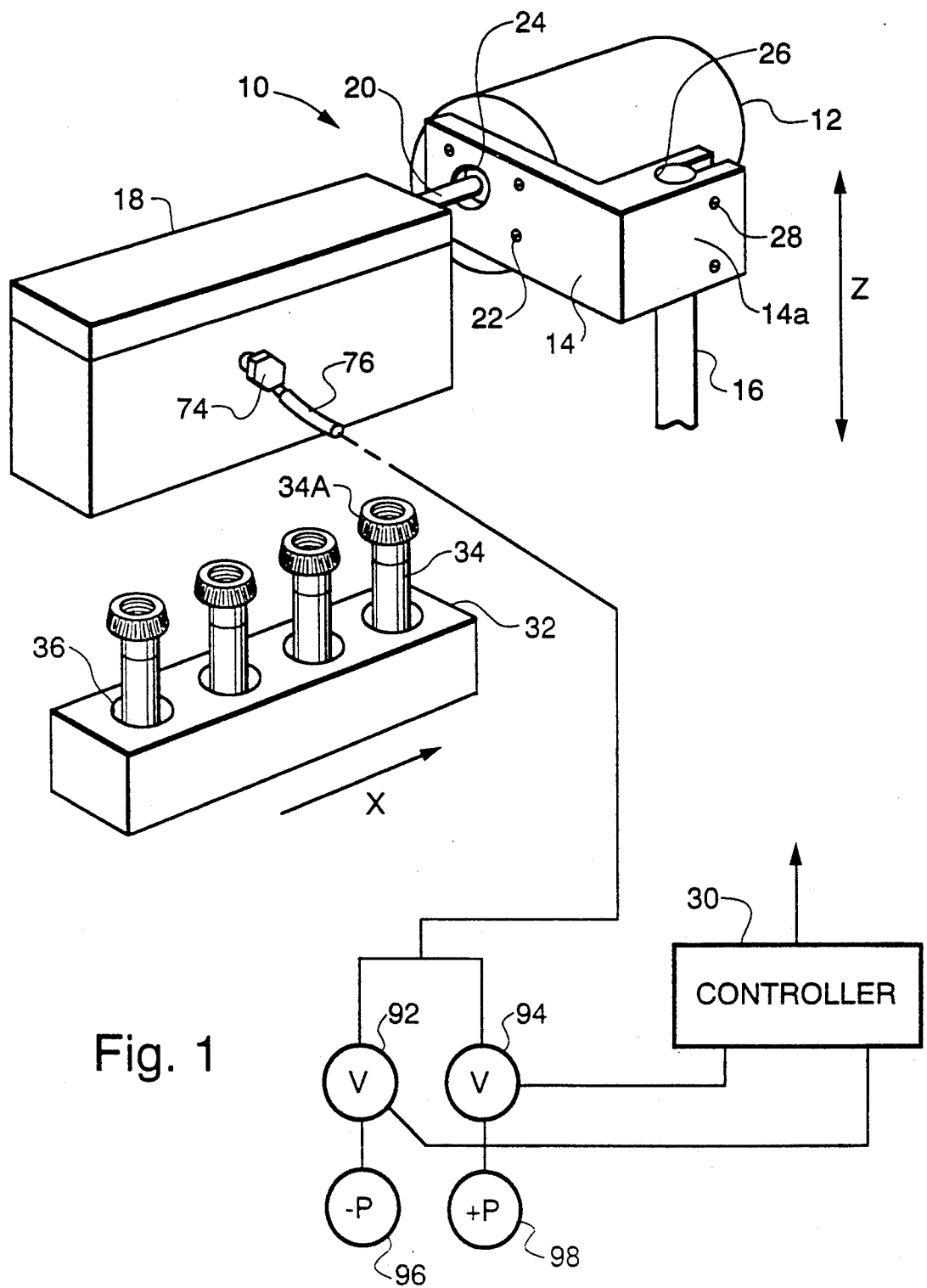
FIG. 1 is a schematic diagram of a prior art mixer device, modified to include a pneumatically actuated sample container holder.

FIG. 1 schematically illustrates a prior art mixer or shaker device, modified in accordance with the principles of the present invention to include a pneumatically actuated holder 18. The mixer device has a head assembly 10 comprising a reversible stepper motor 12, an L-shaped clamp 14, and a vertically extending shaft 16. The holder 18 is mounted on the shaft 20 of the stepper motor 12 so that the holder may be rotated, first in one direction and then the other, through an angle of about 150° as the motor is energized.

The motor 12 is attached to clamp 14 by a plurality of screws 22 and a hole 24 is provided in the clamp so that the motor shaft 20 may extend therethrough. The shaft 16 extends through a hole 26 in a leg 14a of the clamp. The leg 14a is bifurcated from the hole 26 to the edge of the leg and screws 28 are provided for securing the leg to the shaft 16.

The head assembly 10 is movable in the vertical or Z direction by a conventional mechanism (not shown) controlled by a microprocessor-based controller 30. The controller also controls energization of stepper motor 12 to rotate the holder 18, and energization of a conventional conveyor mechanism (not shown) which conveys container carriers 32 in the X direction to a position below the holder 18. Each container carrier 32 has recesses 36 therein and supports one or more containers 34 having caps or closures 34a. The containers may be vacutainers, test tubes or similar sample containers having caps or closures for preventing spillage of a liquid sample contained therein.

Generally speaking, the head assembly 10 is moved to a raised position after which a carrier 32 is moved into position below holder 18. The head assembly 10 is then lowered, and as it is lowered the caps 34a and upper portions of containers 34 enter the holder 18. The holder 18 is then actuated to grip the containers and the head assembly 10 is raised until the bottoms of the containers are clear of the carrier 32. The stepper motor 12 is then actuated to rotate holder 18 and the containers through an arc of about 150 degrees after which it is rotated back through the arc until the containers are again in a vertical position. The arcuate rotation may be repeated one or more times as pre-programmed in the controller 30.

The rotation of the holder and container, first in one direction and then the other, shakes and mixes the sample fluids in the containers 34. After the mixing is completed, the head assembly 10 is lowered so that the containers are again received into the carrier 32. The holder releases the containers and the head assembly 10 is raised so that the holder 18 is above the tops of the containers. The conveyer mechanism is then actuated to move the carrier 32 from underneath the holder and position another carrier in its place. This completes one mixing cycle and the device is ready to repeat the mixing cycle using a new group of containers.

For the sake of simplicity, FIG. 1 shows a carrier 32 having only one row of container-receiving holes 36. However, carriers having more than one row of holes may be used. In the latter case, the controller 30 is programmed to index the conveyor mechanism which transports the carriers by the distance between centers of adjacent rows of holes after each mixing cycle and another carrier is moved into position only after all the samples in a preceding carrier have been mixed.

Figure 2:
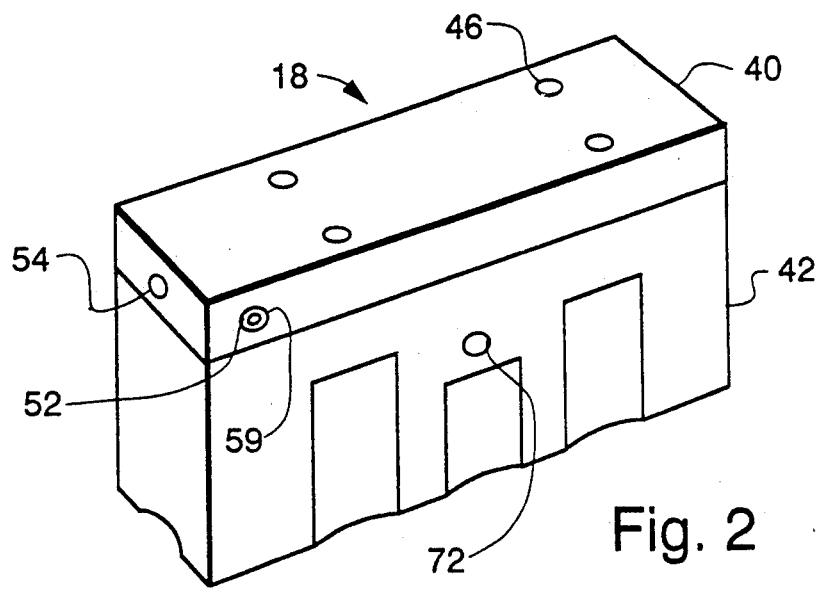
FIG. 2 is a perspective view of the holder.
Figure 3:
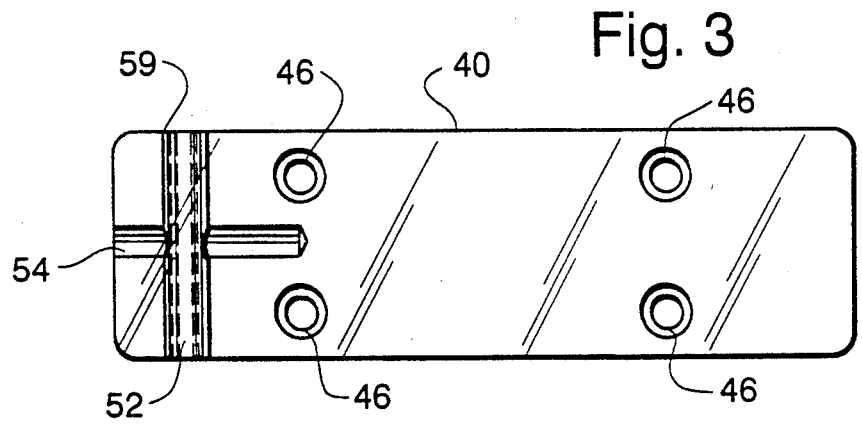
FIG. 3 is a top view of the holder cap.
Figure 5:
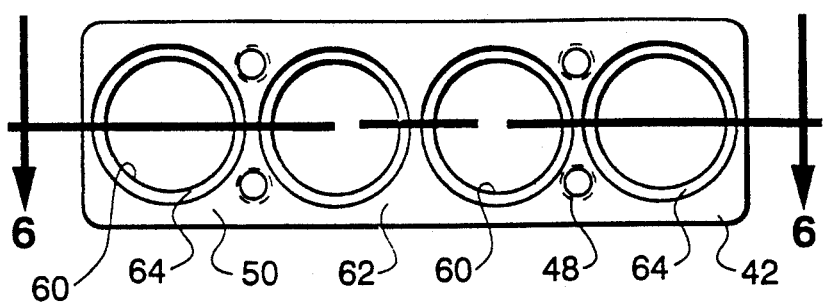
FIG. 5 is a top view of the holder body.
Figure 6:
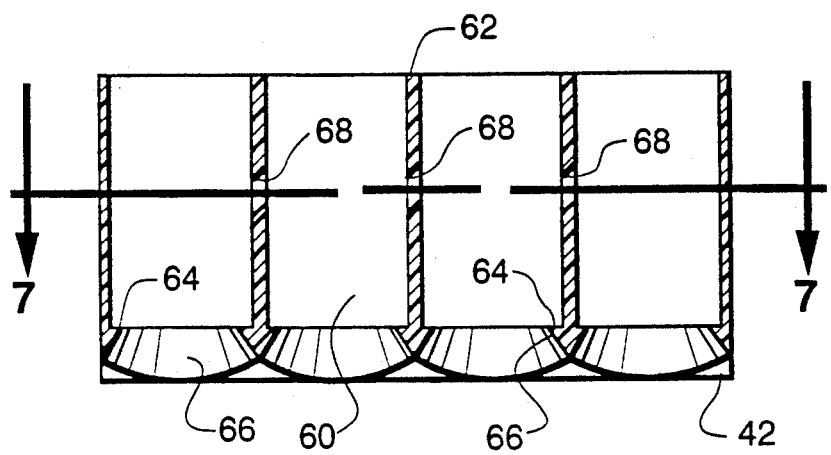
FIG. 6 is a sectional view of the holder body taken along the line 6—6 of FIG. 5.
Figure 7:
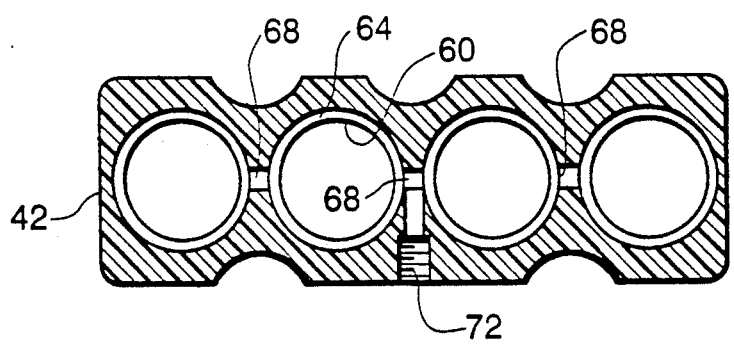
FIG. 7 is a sectional view of the holder body taken along the line 7—7 of FIG. 6.
Figure 8:
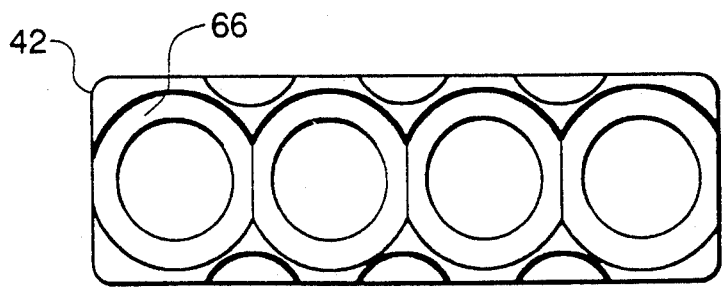
FIG. 8 is a bottom view of the holder body.

According to the present invention, the holder 18 utilizes fluid actuated grippers for gripping and holding the containers 32 as they are shaken. As shown in FIG. 2, the holder 18 comprises a cap or cover 40 and a body 42. The cap has a plurality of holes 46 extending through it from top to bottom, the holes being counter-bored from the top as shown in FIG. 3. A like plurality of threaded holes 48 (FIG. 5) are provided in the top surface 50 of body 42. The cap 40 is secured to body 42 by screws (not shown) which extend through holes 46 and engage threads in holes 48.

The cap 40 is provided with a hole 59 (FIG. 3) extending from one side of the cap the opposing side. A metal insert 52 (FIG. 2) is press-fit into hole 59, the insert being internally threaded from both sides. A hole 54 is drilled into one end of cap 40 and through insert 52. The shaft 20 of stepper motor 12 is inserted into hole 54. Screws (not shown) are inserted into both ends of insert 52 and tightened against the shaft thereby securing cap 40 and body 42 to the shaft.

Figure 4:
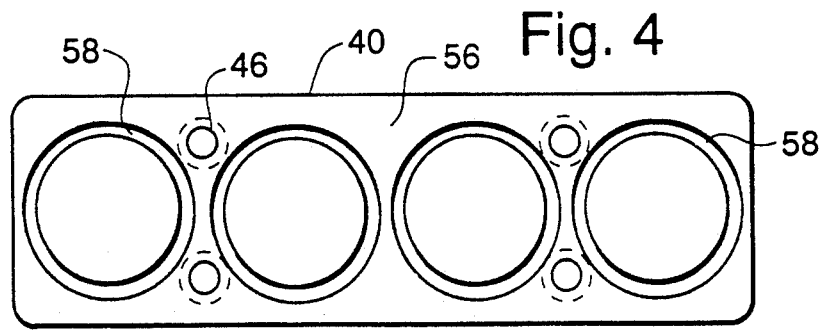
FIG. 4 is a bottom view of the holder cap.

As shown in FIG. 4, the bottom surface 56 of cap 40 is provided with a plurality of annular recesses 58. The number of recesses 58 is equal to the number of containers which may be concurrently held by holder 18, this number being four in the illustrated embodiment. Each recess 58 accommodates an O-ring 88 (FIG. 9) to provide a seal as subsequently described.

FIGS. 5-8 show details of the holder body 42. The body 42 is provided with a plurality of holes 60 extending through the body from the top to the bottom thereof. Holes 60 are counter-bored from the top surface 62 thereby forming inwardly projecting ledges 64 near the bottom of each hole. From ledges 64, the body 42 is flared outwardly at an angle of about 30° thereby forming truncated generally cone-like surfaces 66. The flaring of the body to form surfaces 66 serves two purposes. First, the surfaces 66 form guiding surfaces for directing the tops of container 34 toward holes 60 as the holder 18 is lowered over the containers. Secondly, the angled surfaces provide a wider mouth and thus a better angle for drilling a plurality of openings 68 in the side walls of holes 60.

As subsequently explained, the openings 68 form part of a fluid passage through which positive or negative pressures may be applied to holes 60 to inflate or deflate bladders 82 (FIG. 9) disposed within the holes. One opening 68 is provided for interconnecting each adjacent pair of holes 60. To complete the fluid passage, a further opening 72 (FIG. 7) extends from one side of body 42 to the opening 68 connecting the two centermost holes 60. The opening 72 is threaded to receive an elbow 74 (FIG. 1) having a flexible hollow tube 76 connected thereto.

The cap 40 and body 42 may be made from any suitable plastic material. By way of example only, the cap may be made from clear acrylic resin and the body may be white Delrin or white cast polyurethane.

Figure 9:
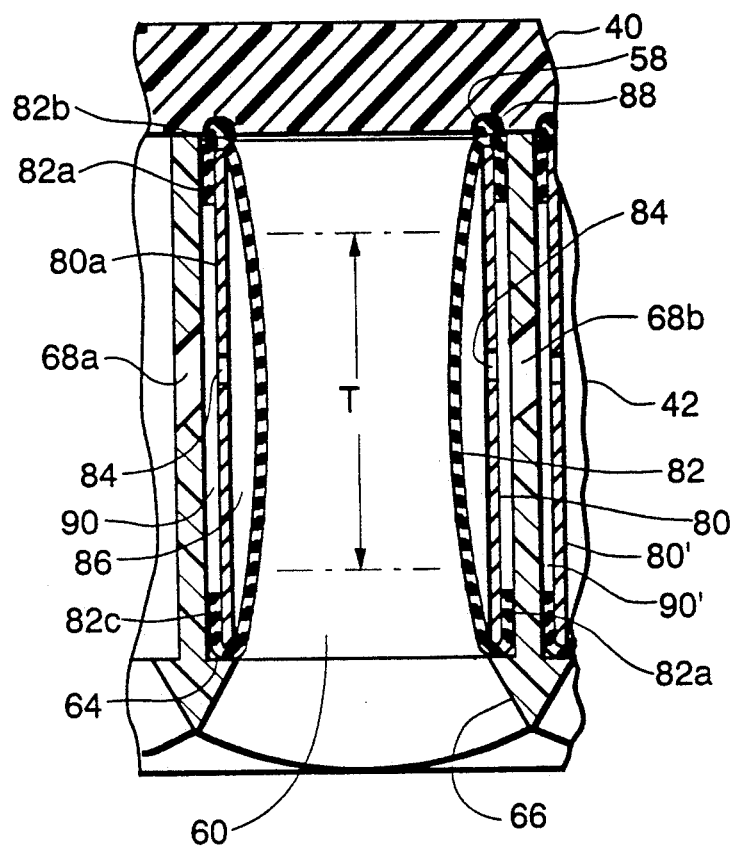
FIG. 9 is a sectional view of a part of the holder illustrating the gripper for one container and its cap.

FIG. 9 is a sectional view of a portion of the holder 18 showing one of the holes 60. Mounted within the hole 60 is a first tubular element 80 and a second tubular element 82. Tubular element 80 is a rigid, preferably metal, cylinder having a plurality of holes 84 extending through its side wall. The tubular element 82 comprises a flexible, preferably silicone rubber, tube or bladder.

The flexible element 82 is longer than the rigid element 80 so that its ends 82a may be radially stretched and folded back over the outer surface 80a of the rigid element. The outer diameter of element 82 is smaller than the inner diameter of element 80 so that when ends 82a are folded back an air-tight, annular region or chamber 86 is formed between the elements. In a practical embodiment the diameter of the flexible element 82, before it is mounted on element 80, may be about ⅜" and the diameter of element 80 may be about ⅞" although these dimensions may be changed to accommodate containers of different sizes. The holes 84 in element 80 serve as a means for applying fluid to, or withdrawing fluid from, the region 86. Preferably, at least four holes 84 are spaced around the periphery of element 84.

After the tubular elements 80 and 82 have been assembled, they are inserted into hole 60 from the top of body 42 after which the O-ring 88 is positioned on top and the cap 40 secured to the body 42.

The inner diameter of the flexible element 82 is chosen such that when the element is folded back over the rigid element 80, the element 82 exhibits a throat region T whose largest diameter is smaller than the diameter of the cap and container it is intended to grip.

The diameter of the rigid element 80 is made smaller than the diameter of hole 60, but larger than the throat bounded by ledge 64, so that the ledge 64 supports elements 80 and 82 within hole 60. When the cap 40 is placed on body 42, the O-ring 88 presses downwardly on the tubular element 82 in the annular region 82b where it folds over the extreme end of the rigid element 80 and this in turn presses an annular region 82c at the lower end of element 82 against ledge 64. An hermetically sealed annular region or chamber 90 is thus formed between the wall bounding hole 60 and the outer surface 80a of rigid element 80. The chamber 90 permits a fluid pressure present at one of the openings 68 to be communicated to the region 86 through all of the openings 84. The chamber 90 also permits a fluid pressure at a first opening 68a to be communicated to an adjacent chamber 90'through a second opening 68b.

During use of the sample container holder 18, positive and negative pressures are selectively applied to the chamber 86 where "positive" and "negative" are relative to the pressure of the ambient environment in which the holder is being operated.

To provide the positive and negative pressures, the opening 72 (FIG. 7) is connected via flexible tubing 76 (FIG. 1) and two electrically controlled valves 92 and 94 to a source 96 of negative pressure and a source 98 of positive pressure. Pneumatic pressures are preferred although hydraulic pressures may be used if desired. Controller 30 selectively produces output signals to open either valve 92 or 94, thereby applying a negative or a positive pressure via tube 76 to opening 72. From opening 72, the pressure is distributed via openings 68, regions 90 and holes 84 to the chambers 86.

As previously stated the flexible element 82 is chosen to have, at ambient pressure in chamber 86, an internal diameter which is less than the diameter of a container which is to be picked up by the holder. The internal diameter of rigid element 80 is chosen such that when a vacuum or negative pressure is applied to chamber 86 to draw the flexible element 82 outwardly toward the internal surface of the rigid element, a sample container and its cap may move freely into the interior of the flexible element. Obviously, the opening bounded by ledge 64 must have a diameter larger than that of a sample container and its cap.

Referring now to FIGS. 1 and 9, the novel holder is operated as follows. After a carrier 32 holding sample containers 34 is positioned under holder 18, the controller 30 actuates valve 92 so that a negative pressure is applied via tube 76, hole 72 (FIG. 7), openings 68, regions 90 (FIG. 9) and holes 84 to chambers 86. The negative pressure in chambers 86 draws the flexible elements 82 outwardly toward the interior surfaces of rigid elements 80.

Next, controller 30 energizes the mechanism to lower the mixer assembly 10. As the assembly is lowered, the caps and upper portions of sample containers 34 are directed toward the interiors of the flexible element 82 by the sloping surfaces 66. Controller 30 then terminates the signal to valve 92 and energizes valve 94 so that a positive pressure is applied to the chambers 86. This pressure forces the flexible elements 82 inwardly away from the internal surfaces of rigid elements 80. As they move inwardly, the elements 82, because they are flexible, engage both the caps and upper portions of the sample containers 34. This reduces the chances of the caps separating from the containers during the lifting and shaking operation which follows.

The controller 30 next energizes the mechanism to raise the holder 18 and the sample containers 34 until the sample containers are free of the carrier 32. The controller then energizes stepper motor 12 to shake the containers 34 by rotating them back and forth through an arc of about 150°. After the containers have been shaken, controller 30 energizes the mechanism for lowering the mixer assembly and as the assembly is lowered the lower portions of sample containers 34 are again received into the recesses 36 in carrier 32.

The controller 30 now deenergizes valve 94 and energizes valve 92 to again apply a negative pressure to the chambers 86. This draws the flexible elements 82 away from the containers and the containers drop slightly under gravity into the carrier 32. With valve 92 still energized, the controller energizes the mechanism for lifting the mixer assembly 10 and as the holder 18 is lifted the flexible elements 82 slide freely relative to the sample containers 34. The mixing cycle is complete once the holder 18 has been lifted above the tops of containers 34 and a new container carrier 32 may be moved into position under holder 18.

The holder of the present invention provides a distinct advantage in that it operates in a fail-safe mode which reduces the chances of dropping a sample container in the event of a power loss or certain failures. Since the internal diameter of flexible elements 82 is less than the diameter of the sample containers 34 when ambient pressure is present in chambers 86, the elements 82 will still grip the containers even when positive pressure is lost because of a power or component failure.

It is readily apparent that because gripping is accomplished by moving flexible elements 82 with a pneumatic pressure, the holder of the present invention is able to grip containers and their caps even though the diameters of the containers and the designs of their caps may vary.

From the foregoing description it is seen that the present invention provides a sample container holder which is simple in its construction, is able to accommodate sample containers of various sizes, reduces the chances of separating containers from their caps, and reduces the chance of dropping containers in the event of a power loss or component failure.

While a preferred embodiment of the invention has been described in specific detail it will be understood that various modifications and substitutions may be made in the described embodiment without departing from the spirit and scope of the invention as defined by the appended claims. Furthermore, although the sample container holder has been described in the environment of a mixer device, it should be understood that the holder may find general utility as a transfer holder for transferring sample containers from carriers to analytical devices or from one stage to another of a multi-stage analytical device.

I claim:

1. A sample container holder for holding at least one container, said holder comprising:
    a body having a plurality of holes extending therethrough in which a container is received;
    a cap mounted on said body covering said container and holes;
    first and second tubular elements of different inner and outer diameters disposed within each of said hole,
    said first tubular element being rigid and having an inner diameter larger than the outer diameter of said second tubular element,
    said second tubular element being flexible and disposed within the first tubular element with first and second ends of the second tubular element being folded back over first and second ends of the first tubular element so as to form an hermetically sealed chamber between said first and second tubular elements;
    said first tubular element and said body having openings therein comprising a fluid passage through which a negative or a positive pressure may be applied to said chamber to increase or decrease, respectively, the inner diameter of said second tubular element whereby a container may be received into a region bounded by said second tubular element when a negative pressure is applied, said container being gripped by said second tubular element when a positive pressure is applied.

2. A sample container holder as claimed in claim 1 wherein the inner diameter of the second tubular element is smaller than the outer diameter of the container to be received therein whereby a container is held by said second tubular element when said chamber is at ambient pressure.

3. A sample container holder as claimed in claim 1 wherein said body has an inwardly projecting ledge around said hole at a first end thereof, said second tubular element, where it folds over the first end of the first tubular element, abutting said ledge, and an O-ring disposed between said first and second tubular elements and said cap pressing said O-ring against said second tubular element where it folds over the second end of the first tubular element, whereby said body and said first tubular element bound an hermetically sealed passage communicating with the openings in said body and said first tubular element.

4. A sample container holder as claimed in claim 3 wherein said body and said cap have generally flat mating surfaces and said cap has an annular recess facing said body for locating said O-ring.

5. A sample container holder as claimed in claim 3 wherein said body is cut away below said ledge so as to form a surface sloping downwardly and outwardly of said hole, said surface directing a container being received toward the region bounded by said second tubular element.

6. A sample container holder for simultaneously gripping a plurality of sample containers and their caps, said holder comprising:
  a body having a plurality of holes extending therethrough for receiving a plurality of sample containers having caps;
  a cover mounted on said body;
  first and second tubular elements of different inner and outer diameters disposed within each of said holes,
  said first tubular elements being rigid and having an inner diameter larger than the outer diameter of said second tubular elements,
  said second tubular elements being flexible and disposed within the first tubular element with first and second ends of the second tubular elements being folded back over first and second ends of the first tubular element so as to form hermetically sealed chambers between the first and second tubular elements;
  said first tubular elements and said body having openings therein comprising a fluid passage through which a negative pressure may be applied to said chamber to increase the inner diameter of said second tubular element whereby containers and their caps may be received into regions bounded by said inner diameters, or a positive pressure may be applied to said chamber to cause said second tubular elements to grip the containers and their caps.

7. A sample container holder as claimed in claim 6 wherein the inner diameters of the second tubular elements are smaller than containers and caps received therein when the pressure in said chambers is ambient pressure.

8. A sample container holder as claimed in claim 7 wherein the openings in said body include first openings connecting adjacently located pairs of said holes, and a further opening extending from one of said first openings to an exterior surface of said body.

9. A sample container holder as claimed in claim 7, further comprising pressure control means connected to said fluid passage for selectively applying a negative pressure to said chambers, and means for causing relative motion between said body and the containers to be received in said holes while said negative pressure is applied whereby said containers are received into said regions.

10. A sample container holder as claimed in claim 9 wherein said pressure control means comprises means for applying a positive pressure to said fluid passage once containers have been received into said regions.

11. A sample container holder as claimed in claim 10 further comprising means for shaking said body during an interval said positive pressure is applied.

12. A sample container holder as claimed in claim 9 wherein said cover is provided with a hole for receiving a rotatable shaft, and means for securing said cover to said shaft.

13. A sample container holder as claimed in claim 7 wherein said body has an inwardly projecting ledge around each hole at a first end thereof, each second tubular element, where it folds over the first end of a first tubular element, abutting a ledge; and a plurality of seals, said cover pressing said seals against said second tubular elements where they fold over the second ends of the first tubular elements, whereby said body and said second tubular elements bound a plurality of hermetically sealed regions within which said first tubular elements are located.

14. A sample container holder device as claimed in claim 13 wherein said body is cut away below said ledges so as to form surfaces sloping downwardly and outwardly of said hole, said surfaces directing containers being received toward said regions.

* * * * *